US005380269A

United States Patent [19]

Urso

[11] Patent Number: 5,380,269

[45] Date of Patent: Jan. 10, 1995

[54] BACK TREATMENT DEVICE

[76] Inventor: Charles L. Urso, 54 Marivista Ave., Waltham, Mass. 02254

[21] Appl. No.: 952,567

[22] Filed: Sep. 28, 1992

Related U.S. Application Data

[63] Continuation-in-part of Ser. No. 749,873, Aug. 26, 1991, Pat. No. 5,224,924.

[51] Int. Cl.[6] .................................................. A61F 5/00

[52] U.S. Cl. ................................ 602/19; 297/411.31; 602/2; 5/646; 177/144

[58] Field of Search .................... 297/180, 411, 411.31, 297/411.32, 411.33; 602/2, 19; 604/240; 128/24 AA, 24 R, 377, 33; 177/144; 5/646, 647, 846

[56] References Cited

U.S. PATENT DOCUMENTS

| | | | |
|---|---|---|---|
| 563,358 | 7/1896 | Burdick . | |
| 786,081 | 3/1905 | Witek | 177/144 |
| 1,266,367 | 5/1918 | Wilson | 5/646 |
| 1,279,120 | 9/1918 | Kellogg | 297/411.31 |
| 1,706,634 | 3/1929 | Seks | 297/411.31 |
| 2,667,913 | 2/1954 | Dustin . | |
| 2,732,269 | 1/1956 | Astroff | 5/646 |
| 2,850,745 | 9/1958 | Cowell . | |
| 2,906,260 | 9/1959 | Myers . | |
| 3,063,752 | 11/1962 | Moore . | |
| 3,124,328 | 3/1964 | Kortsch | 5/646 |
| 3,528,413 | 9/1970 | Aydt | 5/647 |
| 3,710,807 | 1/1973 | Ferry . | |
| 3,896,798 | 7/1975 | Simon . | |
| 4,078,556 | 3/1978 | Fahim | 128/24 AA |
| 4,175,297 | 11/1979 | Robbins et al. | 297/180 |
| 4,258,706 | 3/1981 | Shank | 128/33 |
| 4,335,725 | 6/1982 | Geldmacher | 297/180 |
| 4,565,409 | 1/1986 | . | |
| 4,655,205 | 4/1987 | Hepp et al. | 128/846 |
| 4,748,972 | 6/1988 | Hasegawa | 128/24 AA |
| 4,753,225 | 6/1988 | Vogel | 128/33 |
| 4,815,732 | 3/1989 | Mahvi . | |
| 4,913,393 | 4/1990 | Wood | 297/411.31 |
| 4,996,978 | 3/1991 | Gingras . | |
| 5,011,139 | 4/1991 | Towley, III . | |
| 5,018,512 | 5/1991 | Dolan . | |
| 5,080,352 | 1/1992 | Freed . | |

FOREIGN PATENT DOCUMENTS

| | | |
|---|---|---|
| 23730/88 | 6/1989 | Australia . |
| 510854 | 3/1955 | Canada . |
| 2410839 | 9/1975 | Germany . |
| 3415737 | 10/1984 | Germany . |
| 678693 | 10/1991 | Switzerland . |
| 599871 | 3/1948 | United Kingdom . |

OTHER PUBLICATIONS

International Search Report, PCT/US 92/07231, URSO, Charles L.

BackSaver Catalogue.

*Primary Examiner*—Richard J. Apley
*Assistant Examiner*—Lynne A. Reichard

[57] ABSTRACT

A back treatment device and method of using is disclosed. The back treatment device includes a chair-like seat, body support members including a pair of movably supported crutches, a pair of movably supported forearm rests and a pair of adjustable exercise handles. Each pair is arranged to relieve upper body weight from the lumbar spine. The movable forearm rests allow arm mobility and hand interaction for doing desk work during the treatment period. Feedback from a spring scale allows the user to accurately control gravity traction. A treatment system provides heat or cold treatments adjustably positioned on a back rest. In an alternative embodiment, a diagnosis system positioned on a back rest can provide information regarding a patient's back.

6 Claims, 11 Drawing Sheets

BACK TREATMENT DEVICE

RELATED APPLICATION DATA

This application is a continuation-in-part of U.S. patent application Ser. No. 749,873, filed Aug. 26, 1991, now U.S. Pat No. 5,224,924.

TECHNICAL FIELD

This invention relates to orthopedic chairs that provide gravity traction, exercise handles, heat, cold, and ultrasonic treatments to the lower back.

BACKGROUND

Low back pain is one of the most common reasons for taking time off from work, for seeking medical attention, and for being hospitalized. Among the maladies resulting in low back pain are herniated disc, degenerative disc disease, osteoporosis, arthritis, strained or sprained muscles and ligaments, and muscle spasm. Diagnosis is difficult and better treatment has been elusive. Surgery is useful in only a very small percentage of cases.

The most common treatment methods include periods of immobilization in bed, bed traction (generally uncomfortable and considered dubious), and exercise. Hanging by the limbs (arms or legs) is also advised by some practitioners.

Although most cases eventually recover, healing is often preceded by a lengthy period of agony due to lack of better treatment. The painful episodes often return and some cases become chronic.

Medical authorities generally agree that pain would be relieved and healing expedited if the upper body weight, supported by the lower back, could be temporarily suspended. A practical method of implementing this for a seated patient has heretofore not been devised. The subject invention, however, achieves that objective and more. Included are body support members that relieve the lumbar spine of having to support body weight. In addition, the support members prevent the compounding compressive pressure caused by contracting back muscles; those that contract to keep a seated person from falling forward. Hence, back pain is relieved from multiple sources; muscles and associated ligaments, root nerves emanating from the spine, facet joints, etc. A patient or user can do desk work, such as operating a desk-top computer keyboard or typewriter during treatment. Also provided by the device are automatic time and temperature controlled heat and cold treatments and ultrasonic treatments. Hence, the excruciating ordeal for an acute back pain patient of having to get on and off of a treatment table is obviated.

SUMMARY OF THE INVENTION

The present invention comprises a chair-like device having body support members including a pair of movably supported crutches, a pair of movably supported forearm rests, and a pair of adjustable exercise handles. Each pair is arranged to relieve upper body weight from the lumbar spine. The movable forearm rests allow arm mobility and hand interaction for doing desk work during the treatment period. Feedback from a spring scale allows the user to accurately control gravity traction. A system having a water heating and cooling unit provides heat or cold treatments by circulating temperature controlled water through a bladder adjustably positioned on a back rest. A timer controls the unit and a pump circulates the water over selective time intervals. An ultrasonic transducer is mounted in the bladder to provide ultrasonic treatments.

Other advantages of the invention will become apparent from consideration of the drawings and ensuing description.

BRIEF DESCRIPTION OF THE DRAWINGS

The accompanying drawings in combination with the description herewith, illustrate features and advantages of the invention. Like reference numerals in different views refer to the same parts. The drawings are intended to illustrate principles of the invention and are not necessarily to scale and in which drawings.

DETAILED DESCRIPTION

Figure 1:
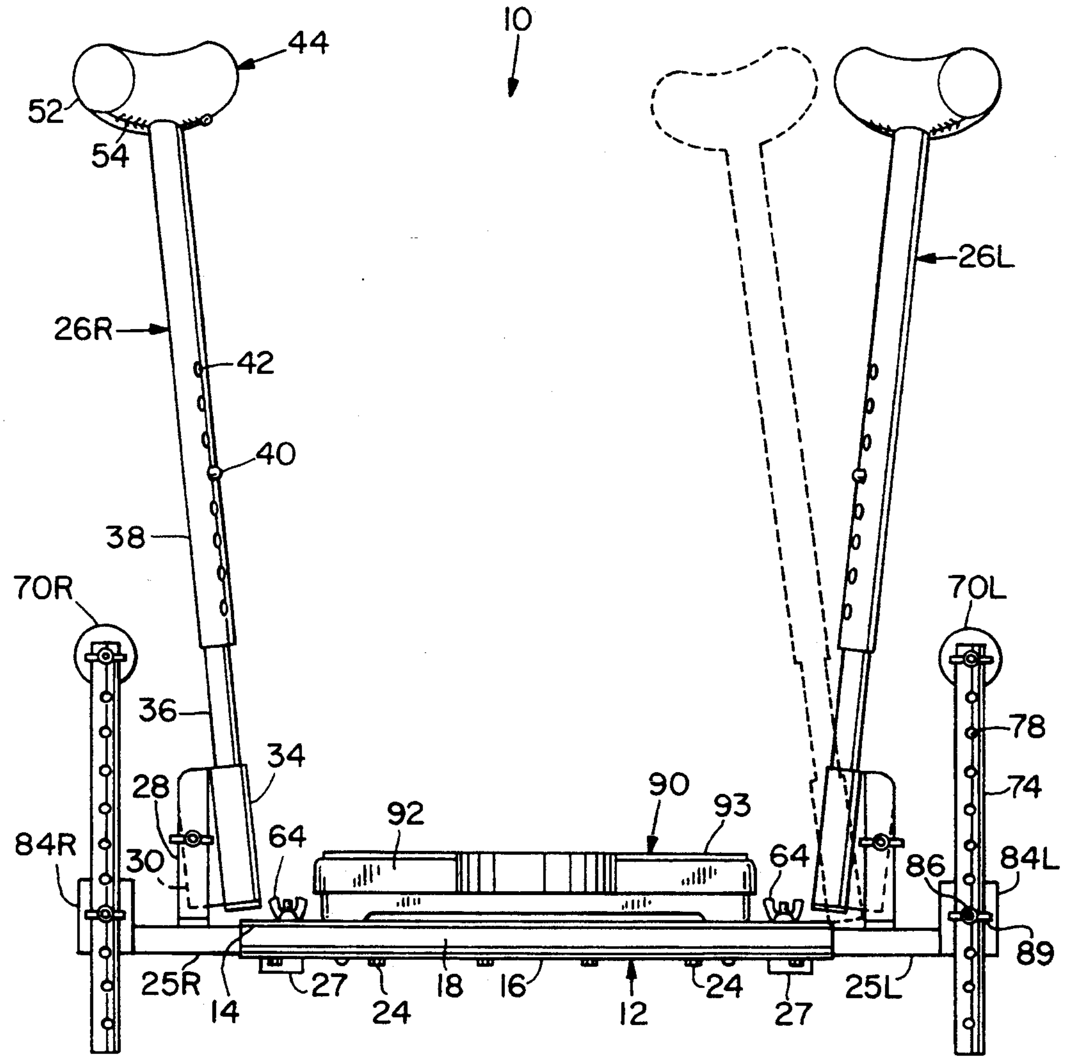
FIG. 1 is a front elevational view of a back treatment device constructed in accordance with the invention, parts being removed for clarity.

A partly constructed back treatment device embodying some of the principles of this invention is identified generally by the numeral 10 in FIG. 1. The device comprises a shallow base 12 having spaced upper and lower rectangular aluminum plates 14, 16. Sandwiched between the plates are two fixed 1×4 inch hardwood boards 18, 20 (FIG. 4) which are spaced from each other. Countersunk flat head machine screws 22 (FIG. 4), passing through the base in bores 23, mate with nuts 24 (FIG. 1) to hold the base together.

The spaced boards and plates define a track which runs longitudinally within the base. The track serves to slidably support two slidable elements 25L, 25R (FIG. 4, 6) comprising hardwood boards. Each element extending from left and right ends of the track, respectively, so that they can slide linearly toward and away from each other.

Figure 4:
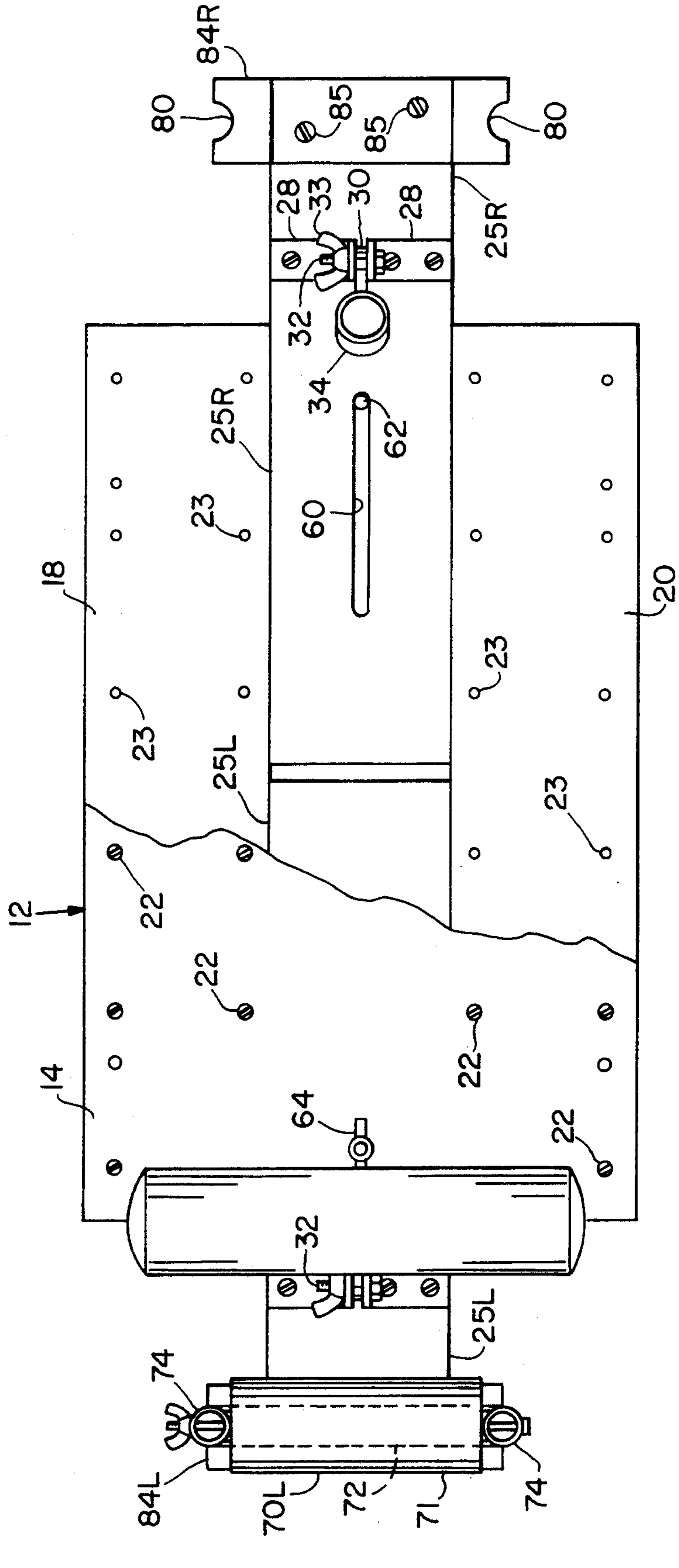
FIG. 4 is a fragmental top view of the device of FIG. 1, wherein more parts are removed.

Each element 25L, 25R is similarly constructed. Therefore, only one is described in detail. As shown in FIG. 4, element 25R includes a longitudinal slot 60 for receiving a screw 62 which passes vertically through a bore in the base 12. The screw 62 is mated to a wing nut 64 (FIG. 1, 6) which serves to lock the element in place after the same is slidably adjusted to a preferred position. Tightening the nut 64 depresses the plates slightly, thereby pressing the plates against the element sandwiched therebetween.

Figure 6:
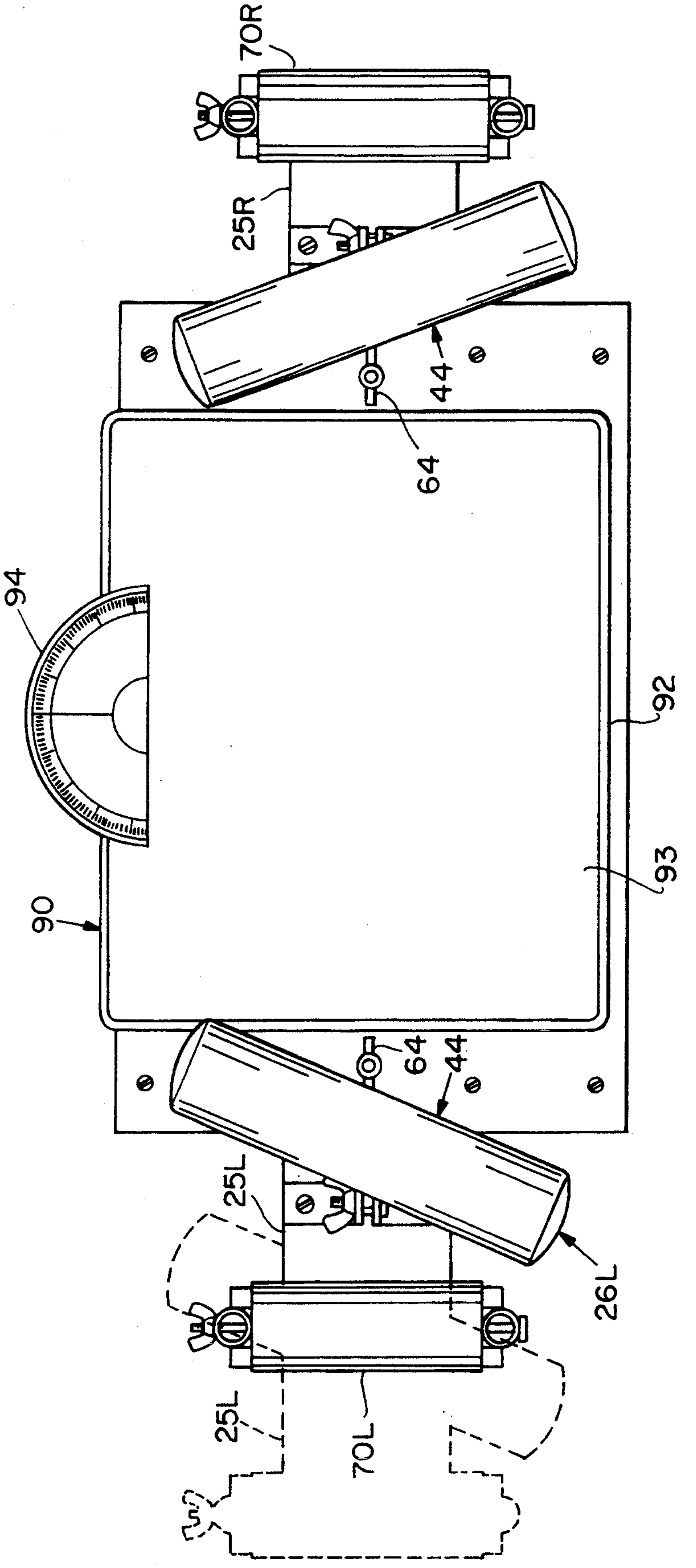
FIG. 6 is a top view of the device of FIG. 1, wherein some movable components are in different positions relative to their positions in FIG. 1.

As best seen in FIG. 1, a pair of adjustable crutches 26L, 26R are mounted on respective outer end portions of the slidable elements. Mounted on the ends of the elements, laterally of the crutches, are a pair of vertically adjustable handles 70L, 70R, respectively. Thus, the right crutch and right handle can slide linearly toward and away from the left crutch and left handle, and vice versa. FIG. 6 shows the left crutch 26L and left handle 70L in a laterally retracted position (solid image) and a laterally extended position (phantom image).

Both crutches are similarly constructed and mounted. Therefore, a detailed description is focused primarily on one crutch. The right crutch 26R includes an inner support tube 36 (FIG. 1) slidably mounted within an outer tube 38 such that the crutch is longitudinally extendible for vertical adjustment. The vertical adjusting means includes a row of holes 42 along tube 38 and a spring button 40, which extends from tube 36, for selectively locking into one of the holes. Other details of the vertical adjusting means are not shown since the method is conventional in crutches used for walking.

Figure 2:
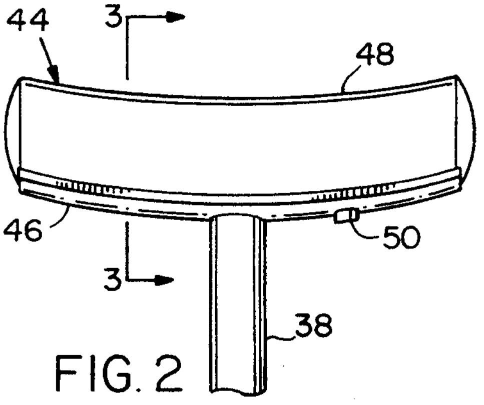
FIG. 2 is a fragmental side view in elevation of a crutch.
Figure 3:
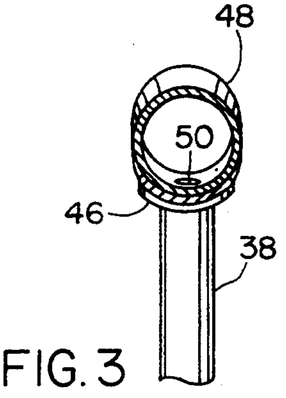
FIG. 3 is a fragmental end view in elevation, partly in section taken vertically along the line 3—3 of FIG. 2.

Mounted to an upper end of tube 38 is an underarm member 44 comprising an elongated rigid boat-like cradle 46 (FIG. 2, 3) welded to tube 38. The cradle includes a concave upper surface for receiving a sausage-shaped inflatable bladder 48 thereon. The underside of the elongated bladder conforms with the cradle. Bladder 48 is comprised of a curved rubber tube closed at both ends and is provided with a filling stem 50 which is similar to that of a football bladder. The stem extends through an aperture in the cradle so that the bladder can be inflated with compressed air introduced through the stem.

Covering the bladder and cradle is a sausage-shaped soft leather cover 52 (FIG. 1) installed by slipping the bladder and cradle through a longitudinal opening in the cover underside. Thus, the soft cover and bladder form an elongated inflatable cushion portion of the underarm member. Laces 54, threaded through lace holes in edge portions of the cover opening, tie the cover tightly in place.

The mounting means for crutch 26R includes a hollow cylindrical sleeve 34 which is closed at its bottom end. Sleeve 34 serves as a bearing which receives tube 36 to pivot therein. A pivot lug 30 extends laterally from the sleeve and is mounted to pivot between a pair of opposed L-shaped outer lugs 28 (FIG. 4) fixed to element 25R with screws. A pivot screw 32, on which lug 30 pivots, passes through aligned apertures in the lugs 28, 30. Wing nut 33 holds the screw 32 in place.

FIG. 1 shows the left crutch 26L in two limiting positions between which the crutch can pivot laterally; an inner position (phantom image) and an outer position (solid image). Hence, the crutches can adjust to a patient supported on the crutches. However, the crutches do not pivot forward or backward so that the patient's spinal column does not move. Each crutch can also pivot about its longitudinal axis as indicated by the relatively different positions of a crutch underarm member comparing FIG. 1, 4 and 6. Thus, when a patient is supported on the crutches, each underarm member adjusts as the patient moves his arms.

Both handles 70L, 70R are constructed and mounted in the same manner. Handle 70L is horizontally positioned and includes a cylindrical urethane foam pad 71 (FIG. 4) surrounding a horizontal cylindrical core 72. Concave end portions of the core receive respective vertical support tubes 74 (FIGS. 1, 4) which are attached thereto by a long screw 87 (FIG. 4) passing through aligned holes in the core and tubes. Each support tube 74 includes a plurality of regularly spaced holes 78 (FIG. 1) passing horizontally through the tubes wherein the holes of one tube are aligned with those of the, opposite tube.

Figure 5:
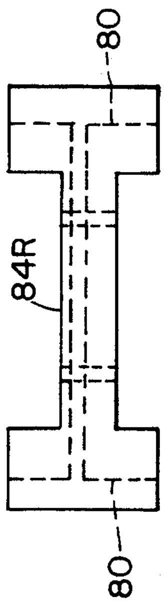
FIG. 5 is a side view in elevation of a track form.

The tubes 74 are slidably supported in a track form 84L. As can be understood from viewing form 84R in FIGS. 4 and 5, the tubes are received in semi-circular tracks 80. Each track form is fixed to a respective element with screws 85 (FIG. 4). A long screw 86 (FIG. 1), passing through aligned tube holes and through the form, holds the tubes in place. A wing nut 89 holds the screw in place and allows easy removal of the screw to be selectively repositioned in another set of tube holes. Thus, the handle can be adjusted vertically to a preferred position.

Another pair of body supporting members which for clarity are shown added to the device in FIGS. 7–10, rather than being included in FIG. 1. The pair comprise forearm rests 140L, 140R, each resembling half of a longitudinally divided hollow cylinder. Each rest includes a rigid outer portion 141 lined on its concave side with a resilient pad 142 which may be foam rubber or plastic foam. The concave surface is intended for receiving and approximately conforming to the underside of the user's forearm.

Each forearm rest is positioned laterally of a respective crutch, below the underarm member. The support means for each rest includes an inner tube 144 capped with a pipe cap 146 welded to an end portion of the tube. A screw 27 (FIG. 8), passing through aligned apertures in the forearm rest and cap, is mated with a nut 148 to hold the components together. A spring 150, inside the tube, compressed between the cap and nut, urges the forearm rest in contact with the cap to form a swivel. As arranged, the forearm rest can pivot about a first pivotal axis; the longitudinal axis of its support means.

The inner tube 144 is slidably received in an outer tube 152 which includes opposing rows of spaced holes 154. A pair of conventional spring buttons 156, extending from the inner tube, are receivable in any selected pair of aligned holes to provide a means for adjusting the height of the forearm rest relative to an associated underarm member.

The lower end portion of the outer tube is capped by a pipe cap 158 welded thereon. Cap 158 is fixed to the center of a U-shaped bracket 160 by a rivet 157 passing through the cap and bracket. The two legs of the bracket are pivotally mounted to lateral sides of respective tubes 74 such that the bracket straddles the tubes and handle. Distal end portions of the bracket legs have aligned apertures which receive the long screw 87 passing through the handle and tubes 74. The bracket pivots on screw 87 so that the forearm rest has a second pivotal axis which is in common with the longitudinal axis of the handle.

Figure 7:
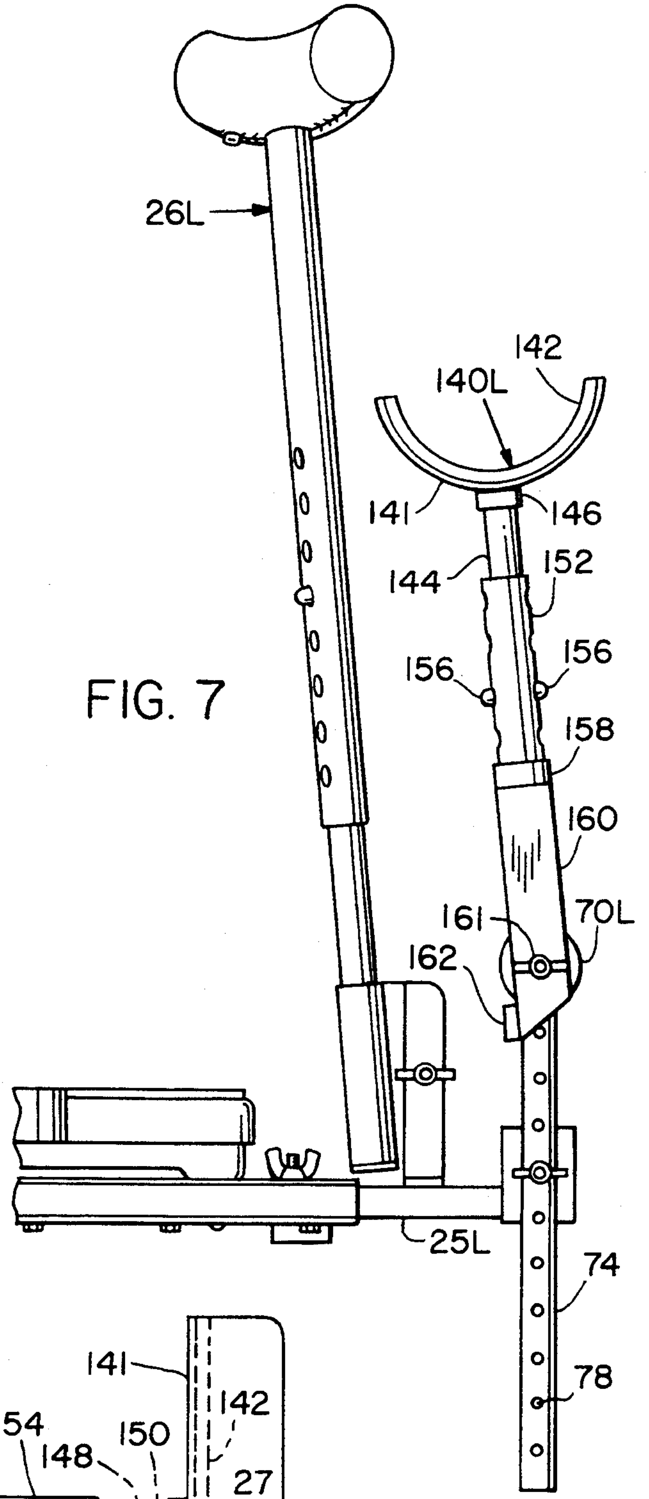
FIG. 7 is a fragmental front view in elevation of the device of FIG. 1, with parts added including a forearm rest in an erect position.
Figure 8:
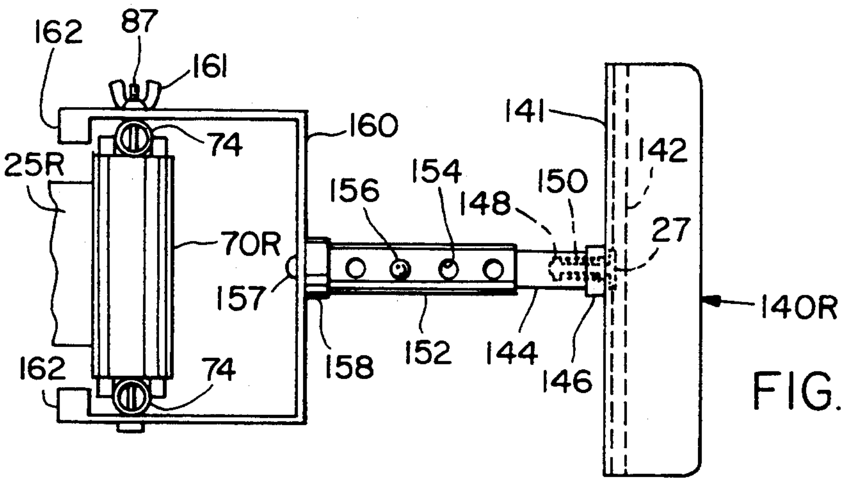
FIG. 8 is a fragmental top view of the device of FIG. 1 with the forearm rest of FIG. 7 in a receded position.
Figure 9:
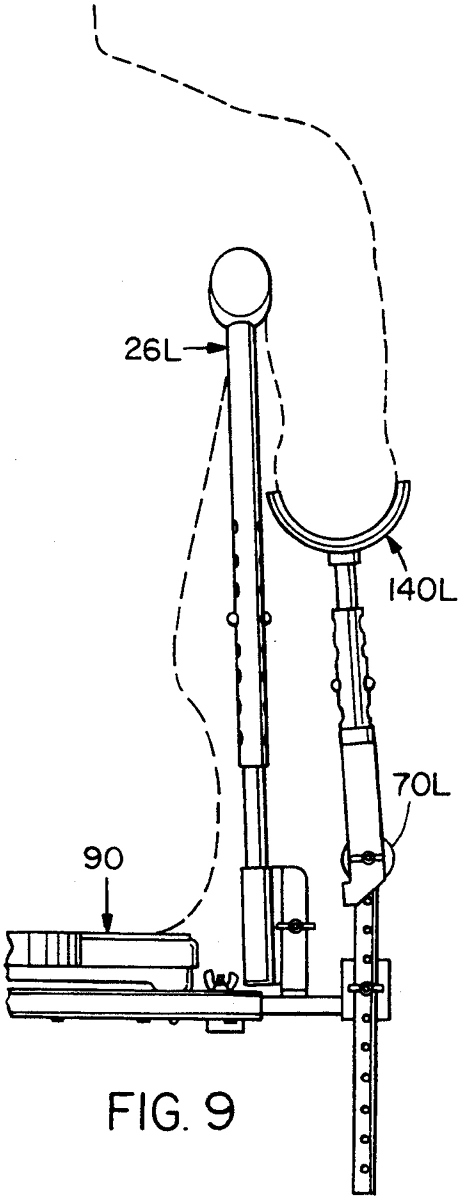
FIG. 9 shows the device of FIG. 7 in use.
Figure 10:
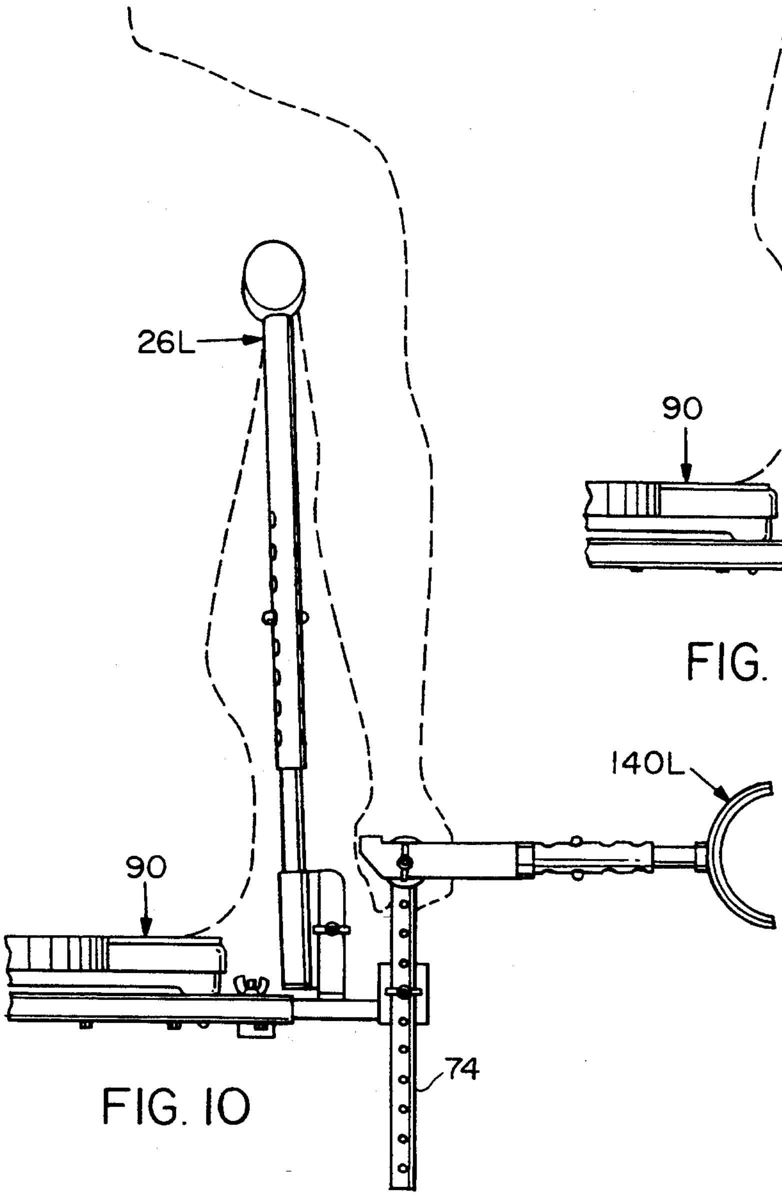
FIG. 10 shows the device of FIG. 7 in use wherein the forearm rest is in a receded position.

Thus, each forearm rest (and its first pivotal axis) can move between an erect position above a respective handle (as shown in FIG. 7 and 9) and a receded position (as shown in FIG. 8 and 10). In the erect position, user body weight can be supported on the forearm rests. In the receded position, the forearm rests are cleared from hindering user access to the handles (forearm rests being positioned laterally of the handles). User body weight can then be supported on the handles. Further downward movement can position the forearm rests below tubes 74. Wing nut 161 can lock a respective rest at any preferred position.

To prevent a respective rest and its support means from exceeding the erect position, a pair of stops 162 contact tubes 74. The stops comprise inwardly directed tabs extending from one side of respective distal end portions of the bracket legs. In the erect position, the center of gravity of the forearm rest and its support means is biased toward the stop side of the bracket. This stabilizes the forearm rest so that locking with the wing nut is generally not necessary. Both forearm rests and their support means are similar in construction and function.

Mounted on the base 12, between the crutches and handles, is a conventional spring scale 90 (FIG. 1, 6). Screws, passing upwardly through the base and into the bottom side of the scale, connect the scale onto the base. Projecting forward from a platform 92 is a quantitative weight indicator 94 (FIG. 6) facing upward for displaying weight sensed by the scale. The scale is positioned relative to the combination such that the indicator projects anteriorly from the main body of the treatment device so that a user sitting on the device can see the indicator through the space normally between the user's thighs. User weight sensed by the scale differs from the user weight supported on the body support members (crutches, forearm rests, handles).

Figure 20:
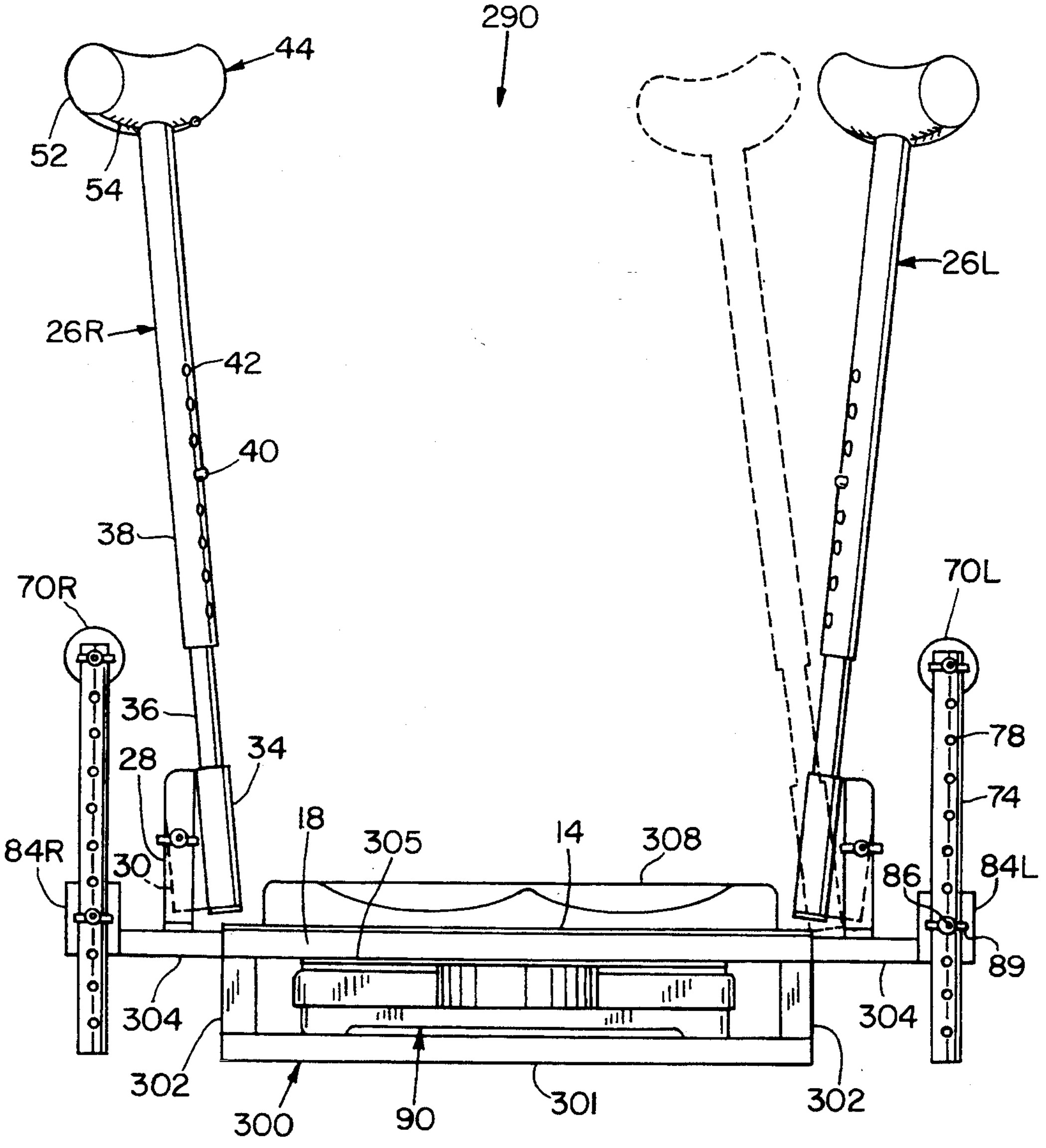
FIG. 20 is a front elevational view of an alternative embodiment of the back treatment device.
Figure 21:
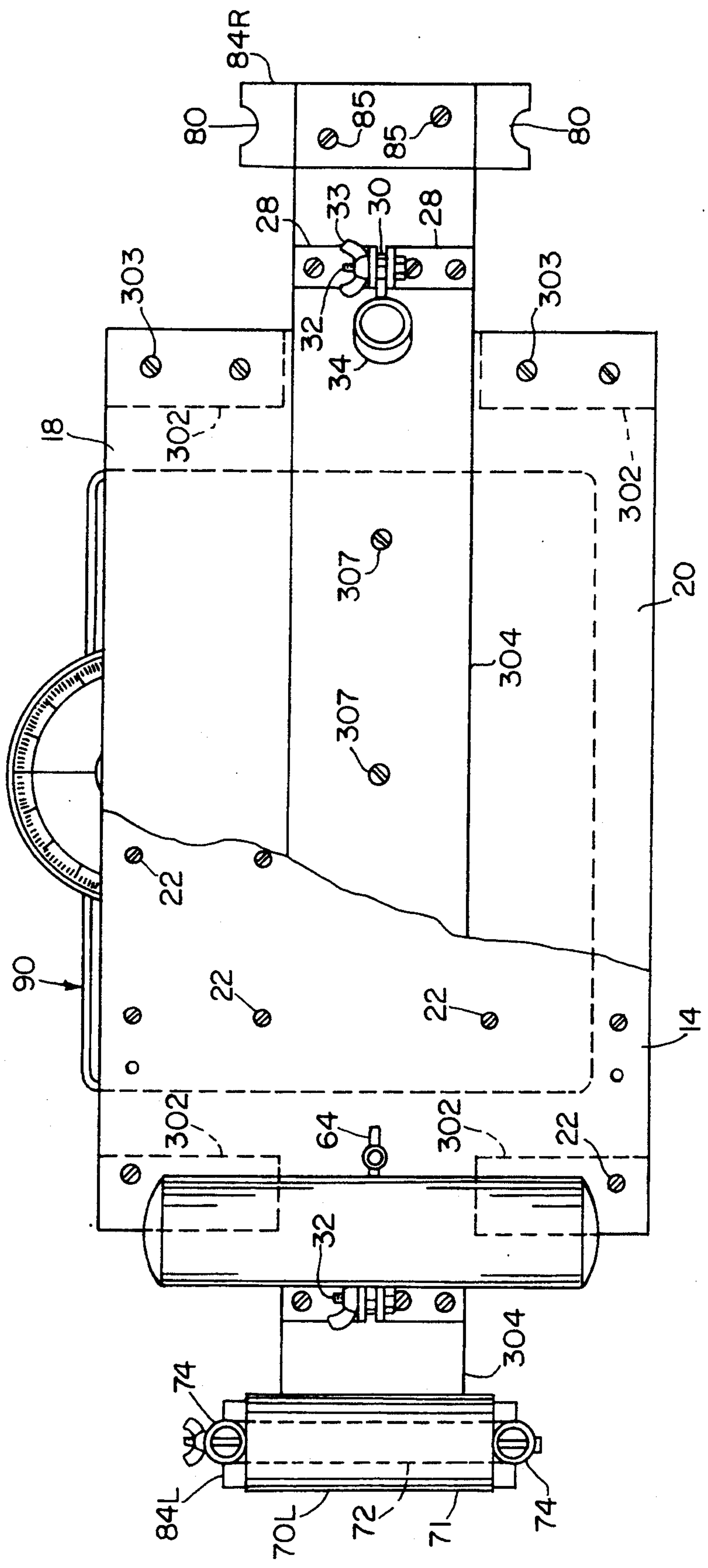
FIG. 21 is a fragmental top view of the device of FIG. 20, wherein parts are removed.

FIGS. 20 and 21 show an alternative embodiment 290 in which the scale 90 is enclosed in a box 300. The box comprises top boards 18, 20 and a rectangular bottom board 301. Positioned between the top and bottom boards are four wooden corner blocks 302 to which the top and bottom boards are fastened with screws 303. Screws (not shown) fasten the base of the scale to board 301. The top of the scale is spaced from boards 18 and 20 because blocks 302 are greater in height than the scale.

Loosely fitted between boards 18 and 20 is a longer middle board 304 having end portions to which the body support members are mounted. A rectangular plate 305 is sandwiched between the scale and a central portion of board 304 by screws 307 which pass through the board, plate, and platform of the scale. Thus, board 304 is fixedly attached to the top of the scale.

For user comfort, a foam rubber seat pad 308 is glued to top plate 14. Unlike embodiment 10, user weight on the seat of embodiment 290 is not sensed by the scale. However, user weight supported on the body support members of embodiment 290 is precisely sensed by the scale and is accurately displayed by the upward facing scale indicator. Knowing that weight is advantageous to the user as is explained hereinafter.

Shown in FIGS. 11–15 are a pair of alternative forearm rests, herein referred to as desk-work forearm rests 200L, 200R. The desk-work rests are especially suitable for use while operating a computer keyboard or typewriter. Each rest and its support means is identical to the other. Each comprises a tapered open shell 202 (FIGS. 11 and 12) shaped for conforming to the underside of the user's forearm, including the elbow. A foam pad 203, having resilient finger-like projections, lines the inside surface of the shell. The aggregate of the projections form a concave surface which receives and contacts the user's forearm. Ambient air around the projections enhances user comfort.

The shell is supported to pivot about aligned pins 204 received in opposed apertures, respectively, in the shell wall. The pins 204 are also received in opposed apertures in a U-shaped gimbal 206. Thus, the shell is pivotally supported such that the concave surface can move within the gimbal. Thrust bearings or washers 207, between the shell and gimbal, encircle each respective pin.

The gimbal 206 is supported to pivot or swivel about a pin 208 (FIGS. 11–13) which passes through aligned apertures in the bottom of the gimbal and in the top or carrying member 210 of a conventional slide 212. Hence, the rest pivots about an erect axis. To reduce friction, a rolling element thrust bearing 209 (FIG. 12) is positioned between the gimbal and slide.

The slide 212 includes ball bearings 211 (FIGS. 13 and 14) retained in a cage 213. A bottom member 214 of the slide is fixedly riveted with rivets 216 to the cross member of a U-shaped bracket 218. When the slide operates, carrying member 210 slides over the bottom member 214 as the ball bearings roll therebetween. Hence, the rest is slidably mounted on the U-shaped bracket.

Figure 11:
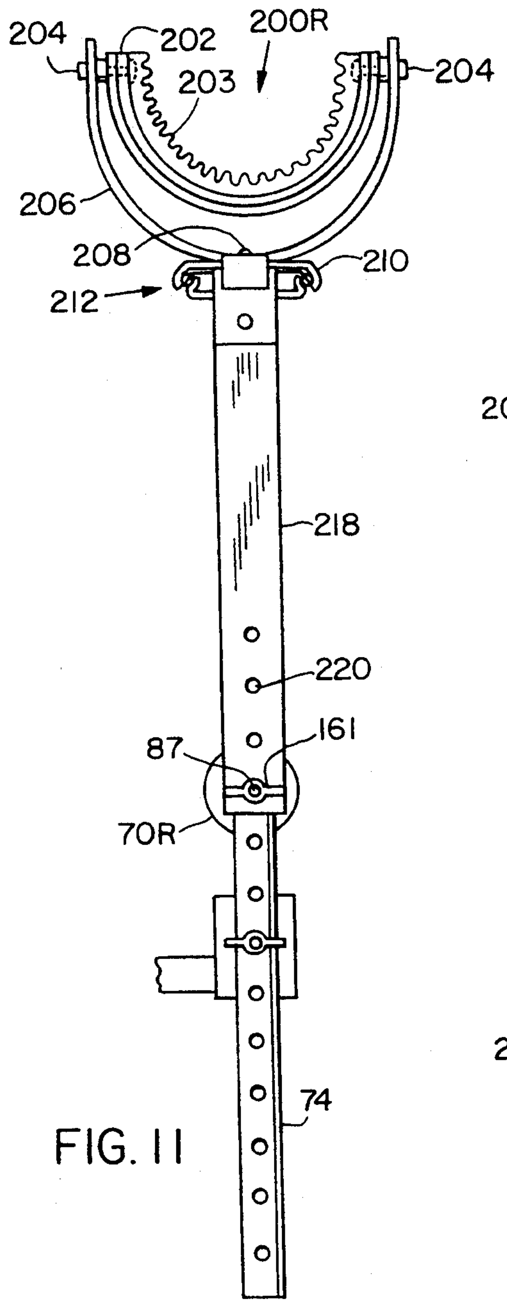
FIG. 11 is a fragmental back view in elevation of the device of FIG. 1, with parts added including a deskwork forearm rest.
Figure 12:
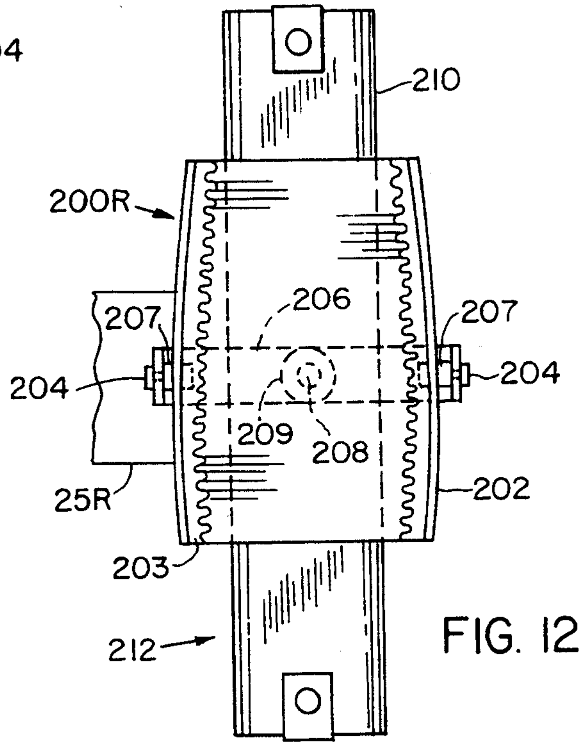
FIG. 12 is a fragmental top view of the device of FIG. 11.
Figure 13:
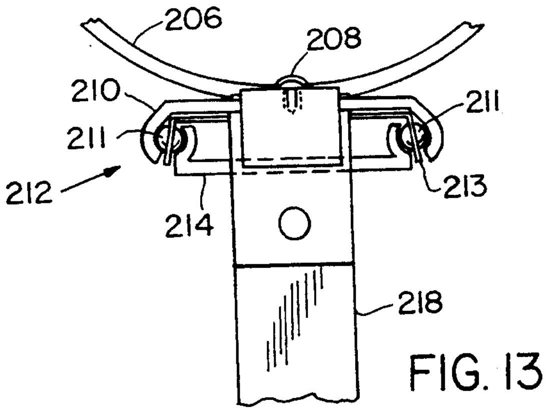
FIG. 13 is an expanded fragmental back view in elevation focusing on a slide portion of the device of FIG. 11.
Figure 14:
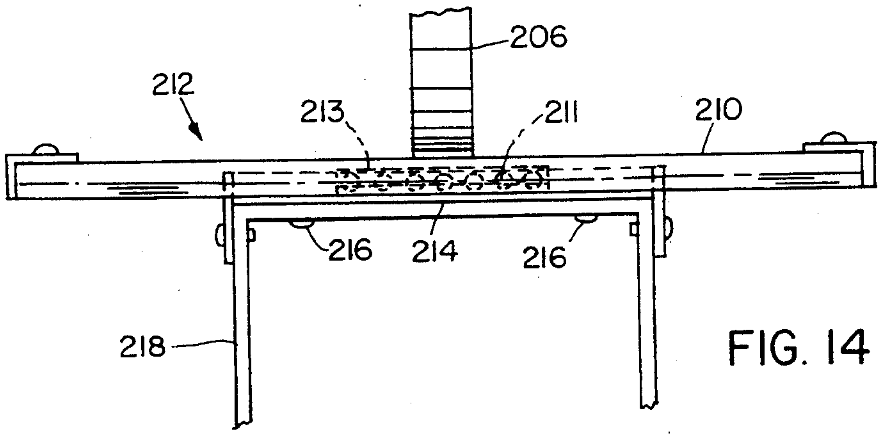
FIG. 14 is a fragmental side view in elevation of the device of FIG. 11.

Bracket 218 is shaped and mounted in much the same manner as bracket 160 and includes legs pivotally mounted to lateral sides of respective tubes 74 (FIG. 11). Thus, the bracket straddles the handle and tubes. End portions of the bracket legs have pairs of aligned mounting holes 220 which selectively receive the long screw 87 passing through the handle 70R and tubes 74. Each bracket pivots on screw 87 so that a pivotal axis of the rest is in common with the longitudinal axis of the handle. The distance between the rest and handle is adjustable by selecting preferred pairs of mounting holes. Wing nut 161 can lock the rest at any preferred position.

Figure 15:
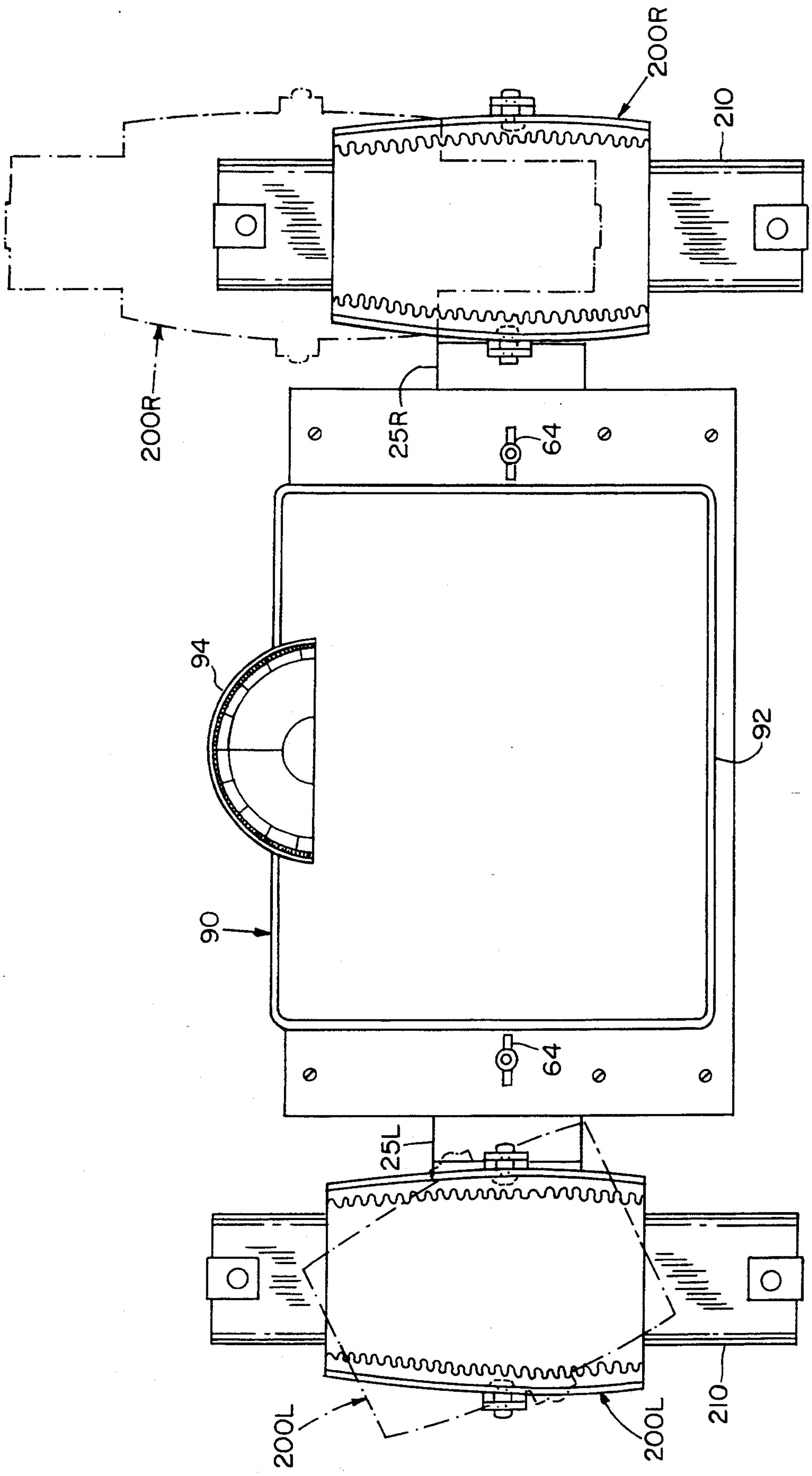
FIG. 15 is a top view of the device of FIG. 1 with parts removed and parts added which include deskwork forearm rests.

The phantom images in FIG. 15 indicate some of the positions to which the desk-work forearm rests can pivot or slide. Each slide carrying member 210, and its associated rest, slide linearly in a horizontal direction which is parallel to the direction of movement of the other carrying member and rest.

From the above description it can also be understood that each desk-work forearm rest is supported to pivot on three axes which are all transverse to each other. The first pivotal axis being the erect axis passing through pivot pin 208. The second pivotal axis being the axis in common with the longitudinal axis of the associated handle. Thus, the first and second axes are analogous to those of rest 140. The third pivotal axis being the axis passing through gimbal pivot pins 204. All three pivotal motions of each rest, in concert with the slide motion, allow the user's arms and hands to move laterally (side to side), up and down, and forward and back. Together, all the support elements for each rest form a free-standing universal mount which supports the rest to move in any direction. Hence, a user can operate a keyboard while his upper body weight is supported on the rests.

Further features of the invention are shown in FIGS. 16–19. They comprise a system which includes a conventional plastic molded chair 230 (FIG. 16) having a seat 232, seat base 233, and back rest 231. Base 233 is fastened to the top of scale 90 using epoxy or fasteners (not shown). The seat includes a small window 234, of any shape, so that the user can see the weight indicator 94 through the space between his or her thighs. A set of conventional tubular chair legs 236 are mounted with conventional mounting brackets 238 screwed to the underside of base 12.

A bladder 240, shaped to fit the lower back of a user, is mounted anteriorly of the back rest. The bladder comprises a thin flexible plastic membrane for containing water. End portions of mounting straps 244 are cemented to the anterior side of the bladder and mid portions of the straps pass over the top of the back rest. Distal end portions of the straps are sewn to hook-and-loop fastening strips 246 (best seen in FIG. 18). The fastening strips are attachable to mate hook-and-loop pads 248 cemented to the posterior side of the back rest. Pads 248 have relatively large areas to provide a choice of locations for attachment of the strips. Hence, the position of the bladder, laterally or vertically relative to the seat, can be adjusted by selective positioning of the fastening strips.

A semi-rigid plastic reinforcement plate 250 is cemented posteriorly of the bladder with waterproof cement. Small apertures through the plate and membrane tightly receive a flanged inlet pipe nipple 252 and a flanged outlet pipe nipple 253, one above the other. The nipple flanges are cemented to plate 250 to seal the edges of the apertures and hold the nipples in place. A slot 254 through the back rest allows the nipples to pass from the bladder to the posterior side of the back rest.

Figure 16:
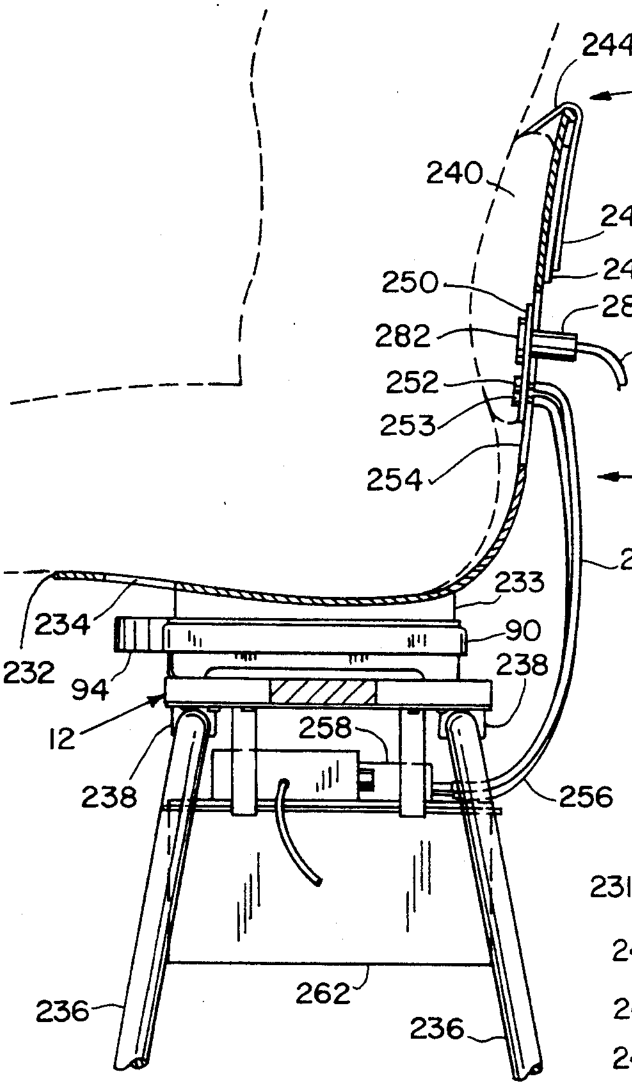
FIG. 16 is a side elevational view of the device of FIG. 1, partly in section, with parts added including a hot, cold, and ultrasonic treatment system.
Figure 17:
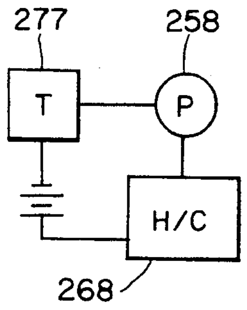
FIG. 17 is a circuit diagram showing how the system of FIG. 16 is electrically connected.
Figure 18:
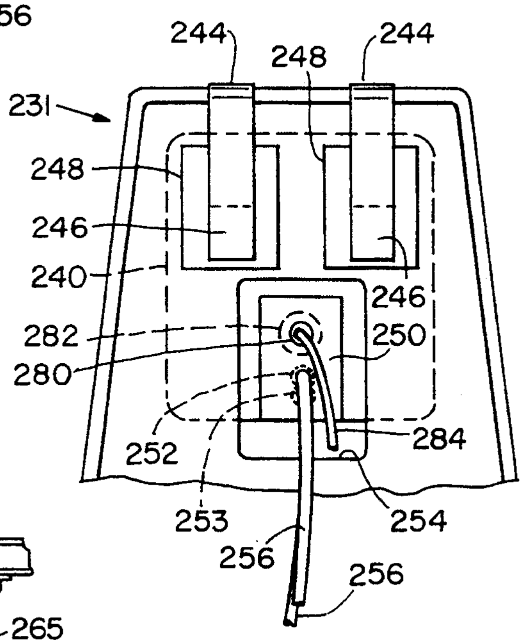
FIG. 18 is a fragmental back view in elevation of the device of FIG. 16.
Figure 19:
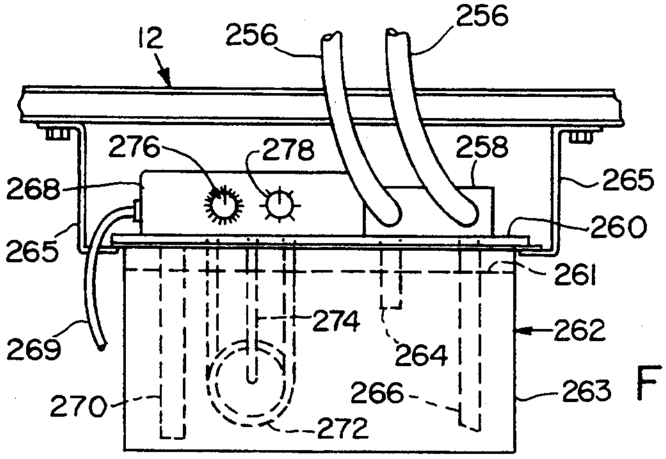
FIG. 19 is a back view in elevation, partly diagrammatic, of a portion of the system of FIG. 16 including a pump and a heating and cooling unit.

Rubber tubes 256 have upper ends connected to the nipples and lower ends connected to a conventional circulator; an electrically operated pump 258 (FIG. 16 and 19). The pump is mounted to the cover 260 (FIG. 19) of a reservoir 262 containing water 261. An inlet pipe 264 and an outlet pipe 266 extend from the pump and into the reservoir water. As arranged, the water can be circulated, by the circulator, from the reservoir to and through the bladder and back to the reservoir in a continuous circuit.

A reservoir pan 263 is supported on brackets 265 screwed to the underside of base 12. A lip extending horizontally from around the top of the pan rests on an L-shaped lower portion of each bracket. The pan can slide off of the brackets for refill.

Also mounted on the reservoir cover is a conventional, electrically operated, portable heating and cooling unit 268. The unit is energized through a power cord 269. Parts of the unit, which extend into the reservoir water, include a heating element 270, a cooling coil 272, and a thermometer 274. Also included in the unit is a conventional thermostat having a control knob 278. The thermostat uses feedback from the thermometer to maintain the water at a temperature selected with the control knob. Water can heated or cooled above or below ambient air temperature.

A conventional timer 277 (FIG. 17) having a control knob 276 (FIG. 19) is built into the heating and cooling unit. The timer is wired to operate the unit and pump during a time interval selected with control knob 276. At the end of the interval, the timer shuts off power to the unit and pump so that the user is not over-treated.

Also included in the system is an ultrasonic transducer 280 (FIG. 16 and 18) received in an aperture passing through the bladder membrane and plate 250. A seal flange 282, tightly encircling the transducer, is cemented to the plate to seal and hold the transducer in place. The transducer passes through the back rest slot and is energized by conventional means through an electric cord 284.

The transducer transmits ultrasonic waves through the water and bladder membrane to penetrate the user's lower back. The bladder membrane conforms intimately with the user's skin to allow transmission of the waves. The position of the transducer is adjusted by adjusting the position of the bladder, using the fastening strips.

Figure 22:
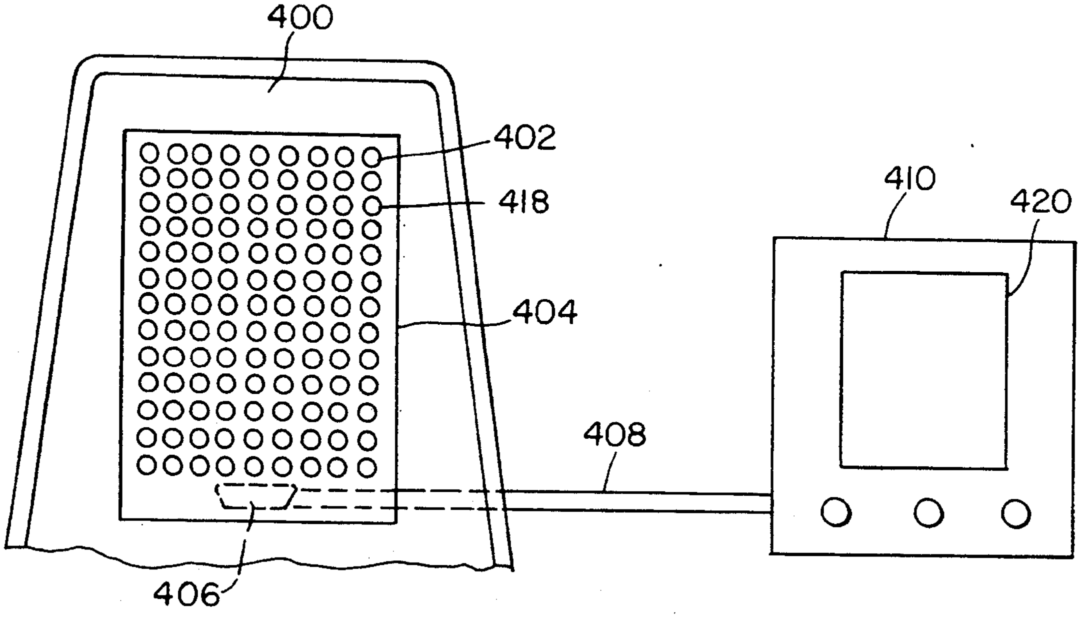
FIG. 22 is a fragmental elevational view of the front of the back rest showing an array of infrared sensors and imaging device.
Figure 23:
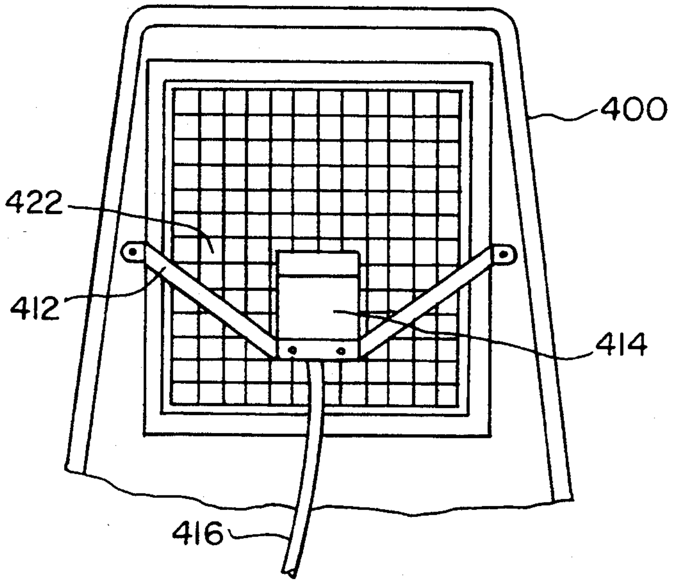
FIG. 23 is a fragmental elevational view of the rear of the back rest showing an infrared camera in position.

Alternative features for the back rest of the present invention used in conjunction with the body support members are depicted in FIGS. 22 and 23. In FIG. 22, an array 402 of infrared sensors 418 are mounted to a printed circuit board 404. The circuit board 404 is mounted to the front surface of back rest 400. Each infrared sensor 418 in the array 402 senses heat generated in a particular region of the back of a patient. Each infrared sensor 418 then provides signals regarding the heat of that particular region of a patient's back to infrared imaging device 410. Imaging device 410 is coupled to each sensor 418 via cable 408 which connects to circuit board 404 at cable connector 406, located at the rear of back rest 400. Imaging device 410 receives the information from the array 402 of infrared sensors 418 and displays a visual representation of that information on screen 420 in a corresponding array format. The visual display on screen 420 of heat generated by a patient's back is helpful in locating areas of a patient's back which are inflamed. Generally, areas of inflammation generate more heat than non-inflamed areas. Furthermore, by correlating a particular region of a patient's back with the corresponding region on array 402, the exact location of inflammation in a patient's back can be determined and treated.

In FIG. 23, infrared camera 414 is mounted to the rear of back rest 400 by bracket 412. Camera 414 views the back of a patient through a window 422 which has a wire grid thereacross. Cable 416 couples camera 414 to imaging device 410 (as in FIG. 22). Camera 414 receives and provides essentially the same information as the array 402 of sensors 418 (FIG. 22) for display upon imaging device 410. Grid window 422 allows regions of inflammation in a patient's back to be located in the same manner as when array 402 is used.

OPERATION OF THE INVENTION

The body support members (crutches, forearm rests, handles) should be adjusted to accommodate the individual user. Upper body weight can be supported on the crutches (positioned under his upper arms) and/or on the handles with his hands positioned thereon. Alternatively, his upper body weight can be supported on the forearm rests alone or in combination with the crutches. The objectives are to relieve the spine of upper body weight and, for some ailments, to accurately induce and maintain spinal traction, The traction is achieved by using the body support members in concert with feedback from the weight indicator 94 as explained hereinafter.

With the device properly adjusted, the user can enhance spinal traction by slightly depressing his shoulders while being supported on at least one pair of body support members. This causes an upward pull on the vertebrae and transfers additional upper body weight onto the body support members. The lower portions of the trapezius muscles, which are involved in the action, are large enough to make the effort easy.

All upper body weight can be kept off the lumbar discs by keeping the weight indicated by the scale at about the difference between his total body weight and the weight normally supported by his lowest lumbar disc. This difference is herein called the traction number. For example, if his total body weight is 140 lbs. and the weight normally supported by his lowest disc is 60 lbs., the traction number is 80 lbs. Thus, keeping the indicator at 80 or less produces a tractional force on the user's spine.

In addition to supporting upper body weight, the body support members avoid the compounding compressive pressure on the lumbar spine do to contracting back muscles; the muscles that keep a seated person from falling forward. Hence, multiple sources of back pain are relieved. Those sources include pain associated with spinal facet joints, muscles and ligaments, and everything effected by irritated root nerves emanating from the spine.

The hot, cold, and ultrasonic treatment system is primarily useful during the acute phase of the ailment. Treatments are administered after properly adjusting the position of the bladder and setting the control knobs. Temperatures and duration of each treatment may be the same as those performed by practitioners on a treatment table. An acute back pain sufferer avoids the excruciating ordeal of getting on and off of the treatment table. Because the system is automatic, a practitioner that treats with the system is free to tend to other patients. Hot, cold, and ultrasonic treatments are believed to work by breaking up muscle spasm pain cycles and by closing pain gates.

While the above description contains many specificities, these should not be construed as limitations on the scope of the invention, but rather as exemplifications of preferred embodiments. Those skilled in the art will envision other possible variations that are within its scope. Accordingly, the scope of the invention should be determined not by the embodiments illustrated, but by the appended claims and their legal equivalents.

What is claimed is:

1. A back treatment device comprising:
- a chair having a seat and a back rest;
- a bladder, for containing liquid, mounted on the back rest; and
- an ultrasonic transducer mounted to the bladder for transmitting ultrasonic waves through the liquid in order to treat back ailments.

2. The back treatment device as defined in claim 1, further comprising means for adjusting the position of the transducer relative to the seat.

3. A back treatment device comprising:
- seat means for supporting a portion of the weight of a user;
- a body support member connected for supporting upper body weight of the user; and
- a scale connected for displaying the amount of user weight supported by said body support member independently of user weight supported by said seat means.

4. A body support device comprising:
- seat means for supporting the buttocks of a user;
- a pair of spaced forearm rests connected to the seat means, each rest having a generally concave surface for receiving a user forearm thereon; and
- a pair of gimbals, each gimbal pivotally supporting a respective rest such that the concave surface moves within the gimbal.

5. A body support device comprising:
- seat means for supporting the buttocks of a user;
- a pair of forearm rests spaced from each other for resting each forearm of the user on a respective rest; and
- a pair of free-standing universal mounts connected to the seat means, each mount including an elongated forwardly directed slide, each slide slidably supporting a respective rest for sliding linearly forward and rearward relative to the seat means and the mount movably supporting the rest for universal movement.

6. The body support device as defined in claim 5, wherein each rest includes a surface comprised of resilient finger-like projections, the aggregate of the projections forming a generally concave surface for receiving the user's forearm thereon.

* * * * *